United States Patent [19]
Questo

[11] Patent Number: 4,505,156
[45] Date of Patent: Mar. 19, 1985

[54] METHOD AND APPARATUS FOR SWITCHING MULTI-ELEMENT TRANSDUCER ARRAYS

[75] Inventor: Warren O. Questo, Orangevale, Calif.

[73] Assignee: Sound Products Company L.P., New York, N.Y.

[21] Appl. No.: 506,499

[22] Filed: Jun. 21, 1983

[51] Int. Cl.³ .............................................. G01N 29/00
[52] U.S. Cl. ...................................................... 73/626
[58] Field of Search ................. 73/626, 625, 628, 641; 128/660; 367/105, 103, 119, 122, 123

[56] References Cited
U.S. PATENT DOCUMENTS

| | | | |
|---|---|---|---|
| 4,224,829 | 9/1980 | Kawabuchi et al. | 73/626 |
| 4,254,662 | 3/1981 | Kuroda et al. | 73/626 |
| 4,442,713 | 4/1984 | Wilson et al. | 73/626 |

*Primary Examiner*—Stephen A. Kreitman
*Attorney, Agent, or Firm*—Weissenberger and Peterson

[57] ABSTRACT

A simple, versatile switching system for ultrasonic transducer arrays uses in-probe concentration and a crosspoint switching matrix, both under the control of a microprocessor in the control unit. The number of crosspoints is kept to a minimum by connecting transducer elements to the pulse delay or receive delay lines in symmetrical pairs; and the high-voltage pulsing is done on the probe side of the switching matrix to allow the use of the same light-duty matrix for both pulsing and receiving.

14 Claims, 9 Drawing Figures

METHOD AND APPARATUS FOR SWITCHING MULTI-ELEMENT TRANSDUCER ARRAYS

SUMMARY OF THE INVENTION

This invention relates to switching systems for transducer elements in ultrasonic diagnostic equipment.

BACKGROUND OF THE INVENTION

In the field of ultrasonic diagnostics, sector scans or linear scans of an object or body under examination may be achieved by using multi-element transducers which remain stationary with respect to body or object. The scan is produced by successively activating groups of elements so as to produce a series of ultrasonic beams which travel sequentially along the length of the transducer. In order to produce a beam which is focused in a focal plane positioned for optimum image information, it is necessary to pulse the various elements of a beam-producing group at slightly different times from one another. Likewise, the echoes received by the various elements of a group need to be delayed by corresponding amounts in order to produce a composite echo indication focused in the focal plane.

The production of the various delays involved in this type of scanning process is conventional and well known. The difficulty arises when large groups of elements must be rapidly switched to produce the travel of the beam. For example, in a scan having 128 separate beam positions, it would usually be necessary to switch a lens of 32 elements to different delay lines varying from 0 to about 800ns in typically less than 25 $\mu$s in order to produce a complete scan for each frame of a TV picture.

Prior art switching systems capable of achieving these results have been highly complex, expensive, and have exhibited little versatility. Specifically, prior art devices have been unable to accommodate different types of transducer arrays and different types of scans without system modification. Also, most prior art devices have required many conductors between the transducer itself and the control unit containing the switching electronics.

SUMMARY OF THE INVENTION

The present invention provides a switching system which is relatively simple and inexpensive, and which is capable of accommodating, without modification, linear and curved transducer arrays; sector scans, M scans, linear scans, and interleaved scans; and multiple-beam echo detection. The invention accommodates all of these arrays and modes with a minimum number of coaxial lines between the transducer probe and the control unit, and with a minimum number of switching elements in the control unit.

The invention accomplishes these purposes by doing three things: first, it concentrates, within the probe, the lines coming from the individual transducer elements into a number of lines corresponding to the number of elements in a group, under the control of a microprocessor in the control unit; secondly, it uses a crosspoint switching matrix, also controlled by the microprocessor, to translate the delay pattern for half of the group into two symmetrical patterns applied to the group as a whole; and thirdly, the high-voltage pulsing of the transducer is performed between the switching matrix and the probe, so as to allow the use of the same switching matrix at low voltage and current levels for both pulsing and receiving.

It is thus the object of the invention to provide an inexpensive, highly versatile switching system for ultrasonic diagnostic transducers through the use of a crosspoint switching matrix and concentrating apparatus.

It is a further object of the invention to provide a switching system of the type described in which the same light-duty switching matrix can be used for pulsing and receiving.

BRIEF DESCRIPTION OF THE DRAWINGS

FIG. 4b(1) is a block diagram of a portion of the switching system of this invention as used with a single beam receiver;

FIG. 4b(2) is the corresponding portion of the system of this invention as used with a dual beam receiver.

DESCRIPTION OF THE PREFERRED EMBODIMENT

Figure 1:
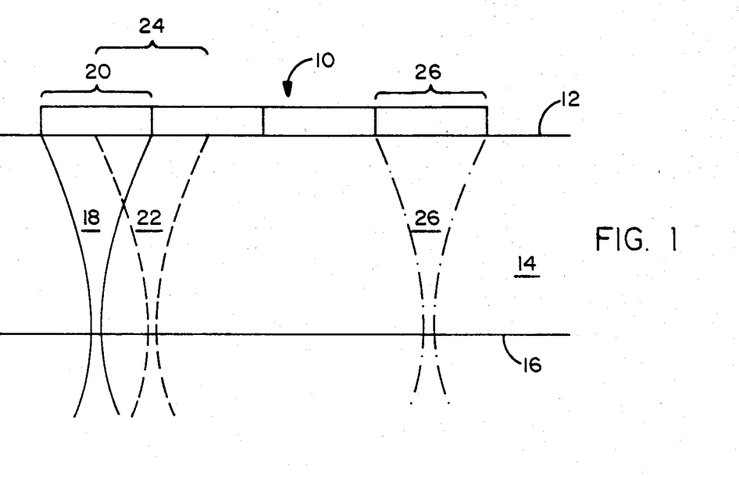
FIG. 1 is a schematic diagram of a linear transducer array illustrating a rectangular scan.

FIG. 1 shows a linear transducer 10 applied to the surface 12 of an object or body 14 to be examined. The area of greatest diagnostic interest in the body 14 lies in the vicinity of the focal plane 16. In order for the ultrasonic beam 18 to be focused at the focal plane 16, the transducer element group 20 is pulsed in such a way that the outer elements of the group 20 are pulsed first and the central element or elements of the group 20 are pulsed last. This manner of pulsing creates a concave wave front which results in focusing at the focal plane 16. At a subsequent time, a beam 22 is produced by the element group 24. It will be noted that the element group 24 has some of its elements in common with the group 20.

The beam production continues sequentially until the last beam 26 of a given scan is produced by the element group 28. Although only three beams have been shown in FIG. 1, it will be understood that a much larger number of closely spaced beams, for example sixty-four or one hundred twenty-eight would normally be used to produce a specific scan.

Figure 2:
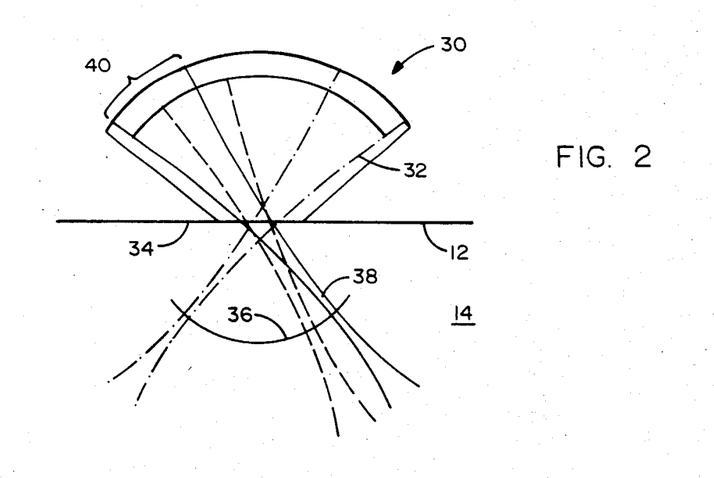
FIG. 2 is a schematic diagram of a curved array illustrating a sector scan.

FIG. 2 shows a sector scan as might advantageously be produced by curved transducer array 30. The curved array 30 is contained within a probe 32 which is applied to the surface of the body 14 by a sound-transparent window 34. The beams produced by the curved transducer 30 are focused in a curved focal plane 36.

A study of FIG. 2 will indicate that, because of the curvature of the array 30, the delay pattern necessary to produce the beam 38 is just the opposite of the delay pattern necessary to produce the beam 18 of FIG. 1. Specifically, in the curved array, the central element or elements of the group 40 must be pulsed first, with the outer elements of the group 40 being pulsed last.

Figure 3:
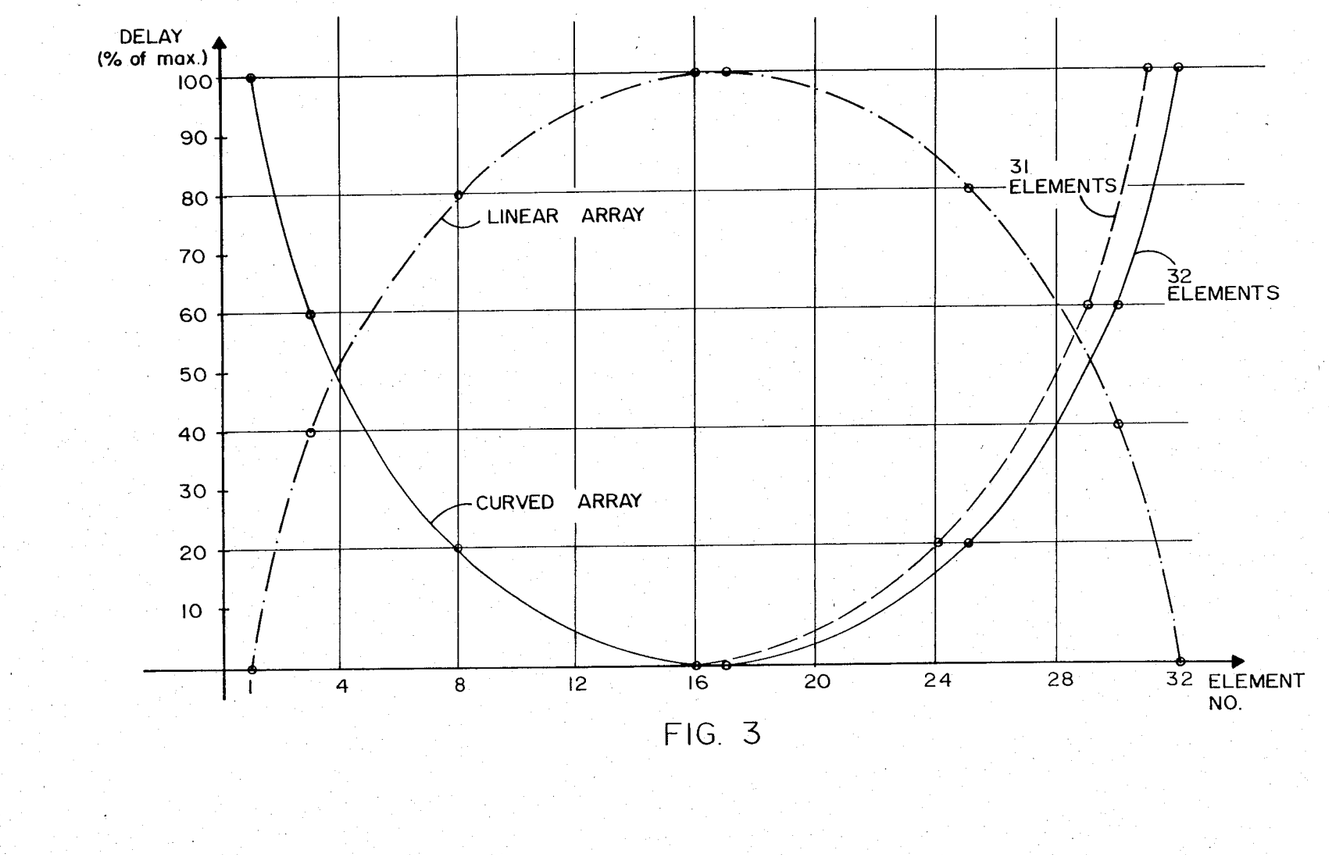
FIG. 3 is a graph depicting the relative delays used for the various elements of a group of transducer elements.

With either type of array, however, the delay pattern is symmetrical about the center line of the beam to be produced. FIG. 3 illustrates this symmetry of the delay pattern. If the number of elements in a group is even (e.g. 32) the delay pattern of elements 1 through 16 will be the mirror image of the delay pattern of elements 17 through 32. On the other hand, if the number of elements in a group is odd (e.g. 31), then the delay patterns of elements 1 through 15 will be the mirror image of the delays of elements 17 through 31, while element 16 will have a delay of its own.

It will also be observed from FIG. 3 that the delay pattern for a linear array is similar to a pattern for a curved array, except for being inverted. Corresponding delays of linear and curved array elements would normally differ only by a constant multiplication factor.

Another type of scan sometimes used in ultrasonic diagnostics is the M scan, which is useful in observing the movement of a specific target toward and away from the transducer. The M scan involves the repetitive activation of the same group of elements (usually the central group of elements). M-scan information can easily be interleaved with another type of scan in the system of this invention by alternating linear or sector scan element groups with the M-scan group in the switching sequence.

Figure 4A:
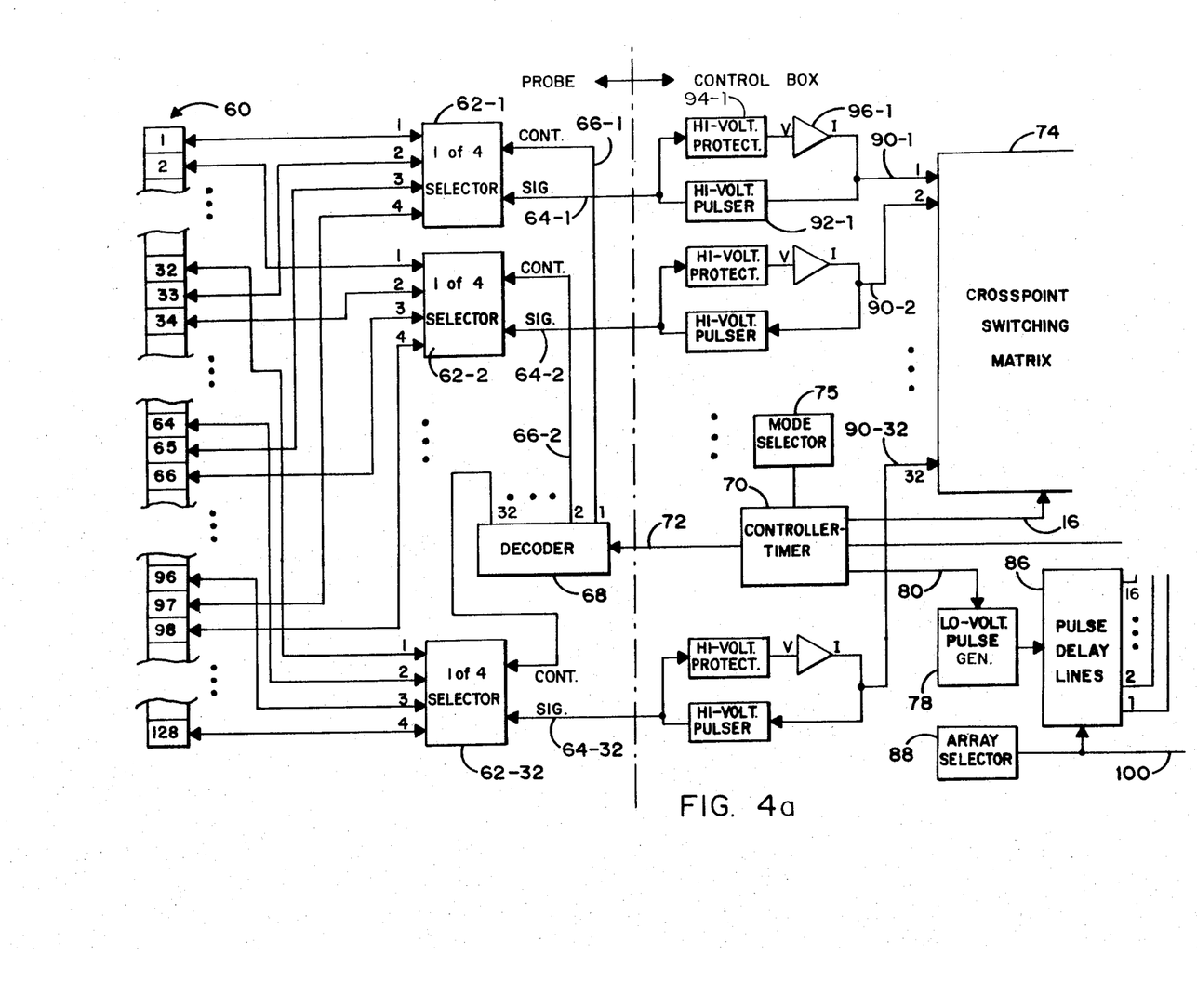
FIG. 4a is a block diagram of the portion of the switching system common to the two embodiments of the invention described herein.

Turning now to FIG. 4a, the transducer is illustrated at 60. It will be understood that the transducer 60 can be either a linear transducer as in FIG. 1 or a curved transducer as in FIG. 2. For the purposes of this discussion, it would be assumed that the transducer 60 has one hundred twenty-eight elements which are to be activated in groups of thirty-two at a time to produce a total of ninety-seven beams per scan. Each of the elements of transducer 60 is connected to a one-of-four selector 62-1 through 62-32. It will be noted that transducer elements Nos. 1, 33, 65, and 97 are connected to selector 62-1, transducer elements No. 2, 34, 66, and 98 are connected to selector 62-2, and so on. The purpose for this connection is that any thirty-two contiguous elements of transducer 60 will always be connected to thirty-two different detectors 62. Thus, by appropriately establishing the internal interconnection in each of the selectors 62, the signal lines 64-1 through 64-32 can be connected to any desired contiguous group of thirty-two elements in the transducer 60.

The internal connections of selectors 62 are controlled by a decoder 68 located in the probe, over control lines 66-1 through 66-32. The decoder 68 is operated in a conventional way by control signals from controller-timer 70 serially transmitted over decoder control line 72. It will be understood that the decoder control 72 may consist of more than one line if timing considerations are such that parallel transmission is required to transmit enough information within the time available.

Figure 4B:
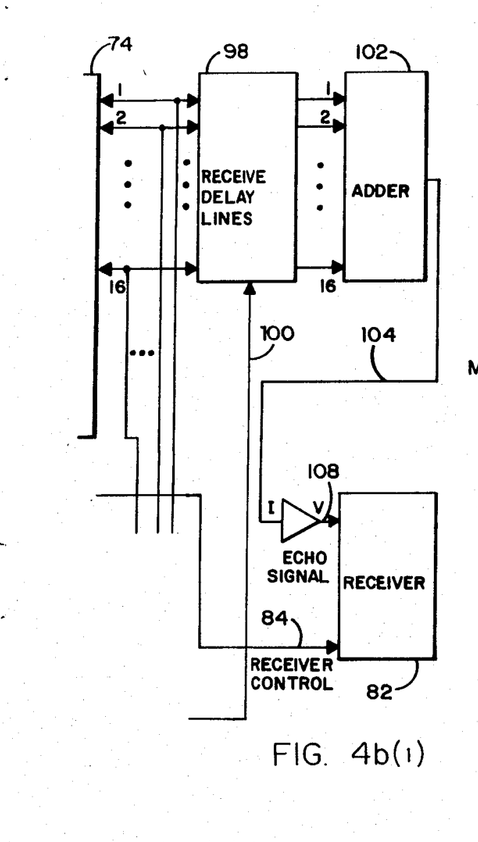

The controller-timer 70 is essentially a microprocessor which has programmed into its memory one or more switching sequences for each of the selectors 62 and for each crosspoint of the crosspoint switching matrix 74. By using mode selector switches 75 to select the appropriate program, the connection patterns of the elements of transducer 60 can be varied to produce any type of desired scan, or even to interleave several different types of scans. Inasmuch as the execution of the microprocessor program is controlled by a master clock internal to the microprocessor, the controller-timer 70 can be used not only to control the decoder 68 over line 72 and the crosspoint switching matrix over data line or lines 76, but can also provide the necessary timing for the pulse generator 78 over pulse control line 80 and of the receiver 82 over receiver control line 84 (FIG. 4b).

The low-voltage pulse generator 78 produces a sequence of low-voltage pulses which are applied to a conventional pulse delay line unit 86. The pattern of delayed pulses appearing at the sixteen outputs of pulse delay line unit 86 can be selected by an array selector switch 88 to fit one of the symmetrical halves of either a linear array group or a curved array group.

Referring to FIG. 4b(1), it will be seen that the sixteen outputs of the pulse delay unit 86 which represent the sixteen differently delayed pulses used in each group of thirty-two transducer elements are applied to the switching matrix 74. In the switching matrix 74, each of the sixteen differently delayed pulses is connected to two of the intermediate signal lines 90-1 through 90-32.

The intermediate matrix lines 90-1 through 90-32 are connected to the intermediate signal lines 64-1 through 64-32, respectively, through a pair of unidirectional parallel paths. In each intermediate line, the outgoing path (i.e. toward the transducer 60) contains a high-voltage pulser 92 which is triggered by the low-voltage pulse from generator 78 to send out a sharp high-voltage pulse to the selected element of transducer 60. The incoming path (from the transducer 60 toward the crosspoint switching matrix 74) contains a high-voltage protection circuit 94 which prevents the high-voltage pulse of pulser 92 from returning to the receiver, and a voltage-to-current converter 96 which converts the voltage-amplitude-modulated echo pulses coming from transducer 60 into current-level-modulated signals which can be added as hereinafter described.

It will be seen that with this system, the crosspoint switching matrix 74 can be used to provide a bidirectional expansion or concentration between the thirty-two intermediate lines and the sixteen corresponding lines from pulse delay unit 86.

Figure 5A:
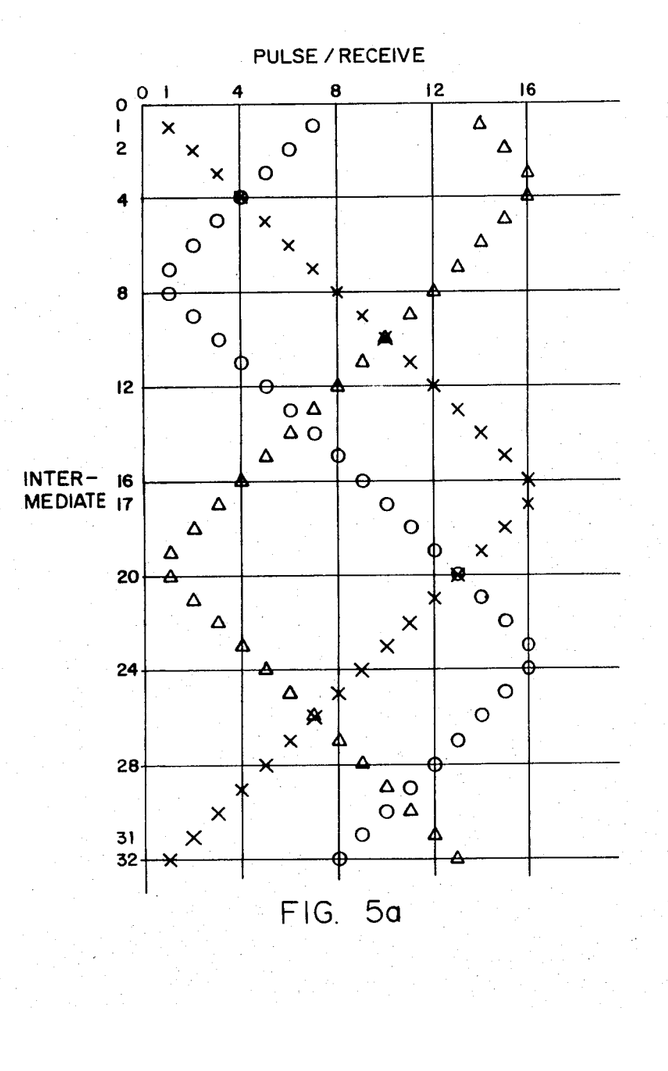
FIGS. 5a and 5b are diagrams illustrating the switching patterns for various groups of elements in the embodiment of FIG. 4b(1)

FIG. 5 illustrates the connection patterns within the crosspoint switching matrix 74 (FIG. 5a) for the first, eighth, and fifty-second beams in the preferred embodiment. It will be noted that the first-beam pattern denoted by x's connects transducer elements Nos. 1 through 32 to the pulse/receive circuits; the eighth-beam pattern denoted by circles so connects elements Nos. 8 through 39; and the fifty-second beam pattern denoted by triangles so connects elements 52 through 83.

Figure 5B:
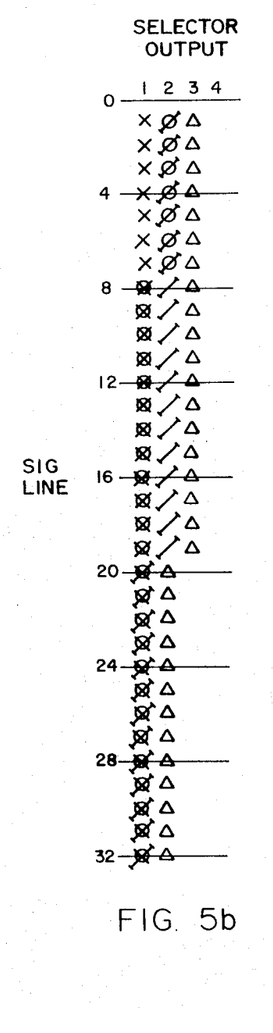

The pattern for the fifty-second beam is the same as for the twentieth beam as far as the crosspoint switching matrix is concerned. The difference lies in the output selections of the one-in-four selectors 62. Whereas the fifty-second beam (triangles in FIG. 5b) uses a combination of outputs 1 and 2, the twentieth beam (asterisks in FIG. 5b) uses the same combination of outputs 2 and 3.

Although the invention has been described herein for clarity in terms of one hundred twenty-eight transducer elements activated in groups of thirty-two, and one-in-four selectors, practical embodiments are more likely to use ninety-six elements with one-in-three concentration (for sixty-four beam equipment) or one hundred sixty elements (for one hundred twenty-eight beam equipment) with one-in-five concentration if thirty-two element groups are used.

Referring again to FIG. 4b(1), the incoming signals from the transducer 60 are added together by pairs to form the sixteen inputs to the receive delay unit 98. This is the reason for the voltage-to-current conversion at converters 96, which causes the echo signal on each of the sixteen lines going into the receive delay unit 98 to be the sum of the echo signals from two symetrically corresponding lines of the intermediate line set 90.

The receive delay unit 98 contains a set of conventional delay lines whose delay pattern is the same as the pattern of the delay lines of pulse delay unit 86. The array selector 88 can be used to switch the receive delay unit 98 between a linear array pattern and a curved array pattern over line 100 in the same manner as pulse delay unit 86.

The appropriately delayed outputs of receive delay unit 98 are added in adder 102 to form a single signal on line 104. This signal can then, if desired, be reconverted to a voltage-amplitude-modulated echo signal in current-to-voltage converter 106. The receiver control line 84 is used to time the operation of receiver 82 in such a way that no echo data is stored during the transmission of the pulses from pulse delay unit 86, and for a sufficient time thereafter to permit ringdown of the transducers and settling of the circuits. The receiver 82 receives the composite echo signal on line 108 and translates it in a known manner into one or more appropriate displays. In this connection, the control line 84 can also be used, if desired, to switch the receiver 82 between an M-scan display and a linear or sector scan display on alternate pulses when these modes are interleaved for simultaneous display on separate monitors.

FIG. 4b(2) shows a modification of the invention to accommodate multiple-beam receiver configurations such as that described in the copending application Ser. No. 506,498 filed on even date herewith. In that configuration, a full group of transistor elements is pulsed to produce an outgoing beam, and partial groups displaced from one another are actuated during the receiving time to provide a simultaneous reception of two echo beams displaced slightly from one another. This technique allows improved target resolution with fewer pulses, as explained in detail in the aforesaid copending application.

Figure 6:
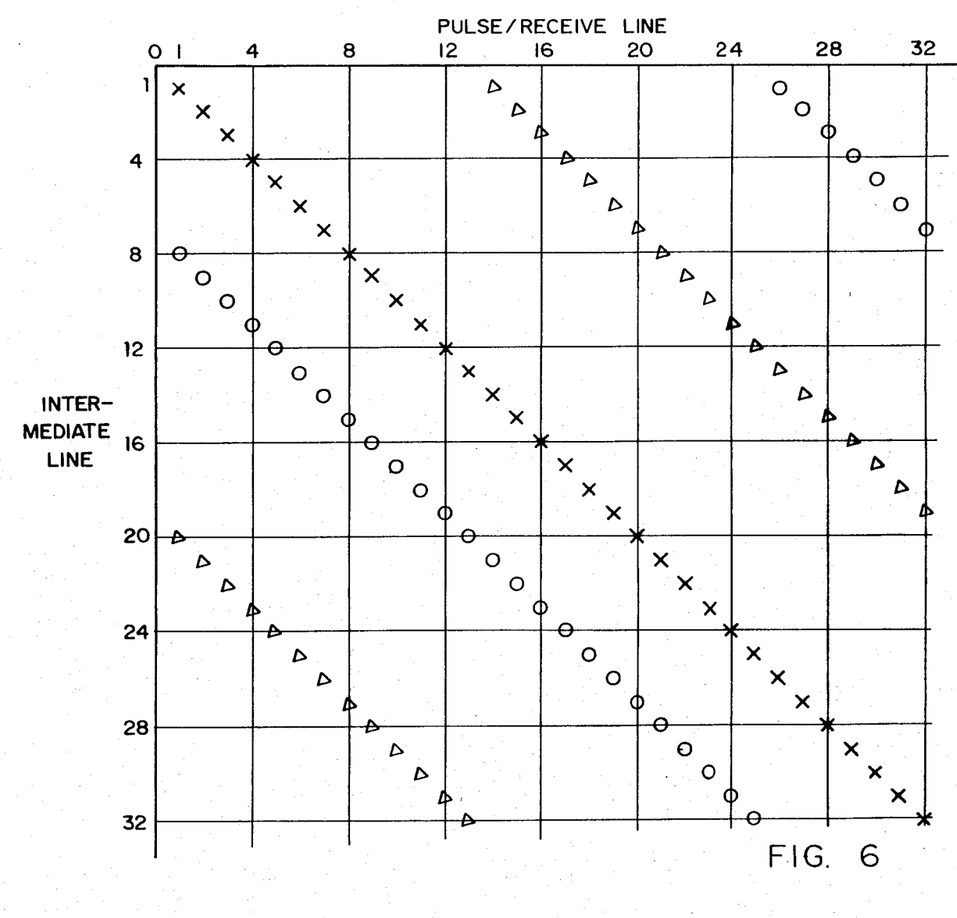
FIG. 6 is a diagram illustrating the corresponding switching patterns for the embodiment of FIG. 4b(2).

In a multiple-beam configuration, a plurality of receive delay units are connected to the crosspoint switching matrix 74 independently of each other. In FIG. 4b(2), a pair of receive delay units 110, 112 is shown. The receive delay units 110, 112 feed into adders 114, 116 respectively, and two separate echo signals are produced by the current-to-voltage converters 118, 120. In a typical embodiment of such a configuration, the connections between the receive delay imputs of FIG. 4b(2) and the intermediate lines of FIG. 4a may, for example, be made in accordance with FIG. 6, in which each "x" marks an interconnection for the pulsing or receiving of the first group of thirty-two elements of transducer 60.

Inasmuch as all thirty-two of the intermediate lines 90 need to be pulsed simultaneously, the outputs of pulse delay unit 86 are connected, respectively, to corresponding switching matrix inputs for each individual receive delay unit. These connections are made through diodes 122, to prevent crosstalk between corresponding inputs of the separate receive delay units.

It will be seen that the above-described switching system provides a simple, efficient, and highly versatile method of interconnecting a transducer array with a simplified pulsing and receiving circuitry. Modifications of the system to accommodate various configurations, particularly different configurations of multiple-beam receiving arrangements, will be apparent to those skilled in the art within the definition of the following claims.

I claim:

1. In an ultrasonic apparatus including a transducer composed of n elements activated in groups of m at a time, the activation of each of said m elements being subject to one of m/2 separate time delays, a switching system for connecting said groups of elements to pulsing means and to receiving means in accordance with a predetermined pattern sequence, said switching system comprising;
   (a) m concentrator means;
   (b) n element lines each connected to one of said transducer elements and to said concentrator means;
   (c) crosspoint switching means;
   (d) m intermediate lines each connected to one of said concentrator means and to said crosspoint switching means;
   (e) m/2 pulse delay means;
   (f) m/2 receive delay means;
   (g) m/2 input-output lines each connected to said crosspoint switching means, to one of said pulse delay means, and to one of said receive delay means; and
   (h) control means connected to said concentrator means and said crosspoint switching means;
   (i) said crosspoint switching means being arranged to connect each of said input-output lines to at least one of said intermediate lines, and said concentrator means each being arranged to connect said intermediate line connected thereto to one of said element lines connected thereto, in accordance with said pattern sequence as determined by said control means.

2. The system of claim 1, in which said crosspoint switching means are arranged to connect each of said input-output lines to two of said intermediate lines.

3. The system of claim 1, in which m is an odd number and m/2 is rounded off to the next higher integer.

4. The system of claim 3, in which said crosspoint switching means are arranged to connect all but one of said input-output lines to separate pairs of said intermediate lines.

5. The system of claim 1, further comprising, in each of said intermediate lines, voltage-to-current converter means and high-voltage pulser means connected in parallel.

6. The system of claim 5, further comprising high-voltage protection means interposed at the input of said converter means within the parallel path of said converter means.

7. The system of claim 1, further comprising pulse generating means operatively connected to said pulse delay means, and receiver means operatively connected to said receive delay means, said control means being also operatively connected to said pulse generating means and said receiver means to synchronize them with said pattern sequence.

8. In an ultrasonic apparatus including a transducer composed of n elements activated in groups of m at a time, the activation of each of said m elements being subject to one of m/2 separate delays, a switching system for connecting said groups of elements to pulsing means and to receiving means in accordance with a predetermined pattern sequence, said switching system comprising;

(a) m concentrator means;

(b) n element lines each connected to one of said transducer elements and to said concentrator means;

(c) crosspoint switching means;

(d) m intermediate lines each connected to one of said concentrator means and to said crosspoint switching means;

(e) at least m/2 pulse delay means;

(f) j independently operable receive delay sets each including k receive delay means, where k is no greater than (m+1)/2;

(g) j sets of k input-output lines, each input-output line being connected to said crosspoint switching means, to one of said pulse delay means, and to one of said receive delay means; and (h) control means connected to said concentrator means and said crosspoint switching means;

(i) said crosspoint switching means being arranged to connect corresponding ones of said input-output lines from each said line set to at least one non-corresponding intermediate line, and each of said intermediate lines to one of said pulse delay means;

(j) said concentrator means each being arranged to connect said intermediate line connected thereto to one of said element lines connected thereto;

(k) said crosspoint switching means and concentrator means connections being made in accordance with said pattern sequence as determined by said control means.

9. The system of claim 8, in which k is an even integer, and said crosspoint switching means connect corresponding ones of said input-output lines from each said line set to a noncorresponding pair of said intermediate lines.

10. The system of claim 8, in which k is an odd integer, and said crosspoint switching means connect all but one corresponding ones of said input-output lines from each said line set to a noncorresponding pair of said intermediate lines, the remaining one of said input-output lines from each said line set being connected to a different single intermediate line.

11. The system of claim 8, in which each of said pulse delay means is connected to a corresponding input-output line of each of said sets.

12. The system of claim 11, further comprising isolating means interposed in the connections of said pulse delay means to said input-output lines.

13. In an ultrasonic diagnostic apparatus including a probe and a control unit located remotely therefrom, said probe containing an array of n transducer elements activated in groups of m at a time, and said control unit containing pulse delay means, receive delay means, and switching means for selectively operatively connecting said delay means to said transducer elements under the control of programmed control means, the improvement comprising:

(a) n element lines in said probe, each element line being connected to one of said elements;

(b) m intermediate lines connecting said probe to said control unit;

(c) concentrator means in said probe connected to said element lines and said intermediate lines for selectively concentrating said element lines into said intermediate lines pursuant to the program of said control means;

(d) decoder means in said probe connected to switch said concentrator means in accordance with commands from said control means; and (e) control line means connecting said decoder to said control means.

14. The improvement of claim 13, in which said commands are transmitted serially over said control line means.

* * * * *